(12) United States Patent
Higashi et al.

(10) Patent No.: US 6,238,085 B1
(45) Date of Patent: May 29, 2001

(54) DIFFERENTIAL THERMAL ANALYSIS SENSOR

(75) Inventors: Robert E. Higashi, Shorewood; Barrett E. Cole, Bloomington, both of MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/224,580

(22) Filed: Dec. 31, 1998

(51) Int. Cl.[7] .............. G01N 25/20; G01K 7/02; G01R 31/20; H01L 35/04

(52) U.S. Cl. .............. 374/10; 374/11; 374/12; 374/13; 374/14; 374/178; 374/179; 438/14; 438/23; 438/54

(58) Field of Search .................. 374/10, 11, 12, 374/13, 14, 179, 178; 438/14, 23, 54

(56) References Cited

U.S. PATENT DOCUMENTS

| | | | |
|---|---|---|---|
| 4,111,717 | * 9/1978 | Baxter | 136/225 |
| 4,677,416 | * 6/1987 | Nishimoto et al. | 338/35 |
| 4,717,786 | * 1/1988 | Thery et al. | 374/179 |
| 4,783,174 | * 11/1988 | Gmelin et al. | 374/11 |
| 4,795,498 | * 1/1989 | Germanton et al. | 374/179 |
| 5,059,543 | * 10/1991 | Wise et al. | 437/974 |
| 5,100,829 | * 3/1992 | Fay et al. | 374/178 |
| 5,104,823 | * 4/1992 | Mand | 437/54 |
| 5,164,359 | * 11/1992 | Calviello et al. | 505/1 |
| 5,181,007 | * 1/1993 | Friese et al. | 338/22 R |
| 5,288,147 | 2/1994 | Schaefer et al. | |
| 5,374,123 | * 12/1994 | Bu | 374/178 |

(List continued on next page.)

FOREIGN PATENT DOCUMENTS

4228484 * 3/1994 (DE) .
137836 * 6/1987 (JP) .

OTHER PUBLICATIONS

Oliveira A et al; "A Digital Differential Thermal Analysis Instrument" Measurement, GB, Institute of Measurement and Control. London, vol. 23, No. 1, Jan. 1, 1998 (1998–01–01), pp. 47–54, XP004129959.

Dennis Schuetzle, Robert Hammerle "Fundamentals and Applications of Chemical Sensors", 1986 American Chemical Society, Wash. D.C., ACS Symposium Series, 0097–6156.

W. Gopel, H. Hesse, J. Zemel "Sensors: A Comprehensive Survey", 1989, Chemical and Biochemical Sensors Part I, vol. 2.

*Primary Examiner*—G. Bradley Bennett
*Assistant Examiner*—Gail Verbitsky
(74) *Attorney, Agent, or Firm*—John G. Shudy, Jr.

(57) ABSTRACT

A sensor having an active sensing material exposed to the substance to be detected and an active reference material that is shielded from the substance to be detected. Thermocouples having a set of junctions proximate to the active sensing material and another set of junctions to the active reference material for measuring the temperatures at the respective materials. The junctions are connected differentially in that a difference of the two temperatures is measured. A heater is proximate and common to the two materials. Heat pulses may be applied to the materials via the heater and the temperatures are measured. If ambient factors or substances affect the active sensing material, its thermal response will be different than that of the active reference material, and a differential pulse-like indication of temperature will be detected. This indication will have certain characteristics of amplitude, shape and time, which indicate an identification of the type and concentration of substance detected by the sensor.

9 Claims, 13 Drawing Sheets

U.S. PATENT DOCUMENTS

| | | | |
|---|---|---|---|
| 5,446,437 | * | 8/1995 | Bantien et al. ......................... 338/25 |
| 5,520,299 | * | 5/1996 | Belcher et al. ......................... 216/66 |
| 5,560,711 | * | 10/1996 | Bu ......................................... 374/178 |
| 5,602,043 | * | 2/1997 | Beratan et al. ......................... 437/3 |
| 5,689,087 | * | 11/1997 | Jack ...................................... 374/179 |
| 5,792,377 | * | 8/1998 | Belcher et al. ......................... 216/87 |
| 5,801,070 | * | 9/1998 | Zanini-Fisher et al. ............... 438/54 |
| 5,804,462 | * | 9/1998 | Liu et al. ............................... 438/54 |
| 5,813,764 | * | 9/1998 | Visser et al. ........................... 374/10 |
| 5,830,372 | * | 11/1998 | Hierold .................................. 216/2 |
| 5,883,009 | * | 3/1999 | Villa et al. ............................. 438/739 |

\* cited by examiner

DIFFERENTIAL THERMAL ANALYSIS SENSOR

BACKGROUND

The present invention pertains to gas and environmental chemical sensors. Particularly, the invention pertains to micromachined integrated chips utilizing heat and thermal transfer characteristics of the gas or substance around an element of the sensor to obtain chemical information about that which is being detected.

SUMMARY OF THE INVENTION

In a thermal modulation technique for sensing, a thermal pulse of an arbitrary shape is applied to the sensor system, and changes in the temperature of the sensing membrane or active material exposed to the environment are monitored as the heat pulse from the active material interacts with the surrounding environment. The thermal pulse is also applied to an active material that is shielded from the environment. Thermocouple junctions proximate to both active materials provide a differential temperature indication between the two materials. The growth and subsequent decay of the heat pulse indicated by differential temperature reflects time dependent changes in the heat transfer characteristics in the gas phase surrounding the sensor. Relevant chemical information is obtained by interpreting the temperature changes of the sensor surface during this dynamic interaction. The power of this detection approach comes from integrating an array of thermally modulated sensors, and combining the selectivity of multiple sorbent phases with the kinetic selectivity of each modulated device. This technique is made possible by the high sensitivity and low thermal mass of silicon-based integrated microcalorimeters.

DESCRIPTION OF THE EMBODIMENTS

The microstructure devices for calorimetric gas sensing have several structural variations. Each of these devices has a laminated heater and thermocouple sensors electrically isolated from the heater. Thermocouples are used for temperature sensing of two items of material, because of their demonstrated low noise, high sensitivity and low offset characteristics.

Figure 1:
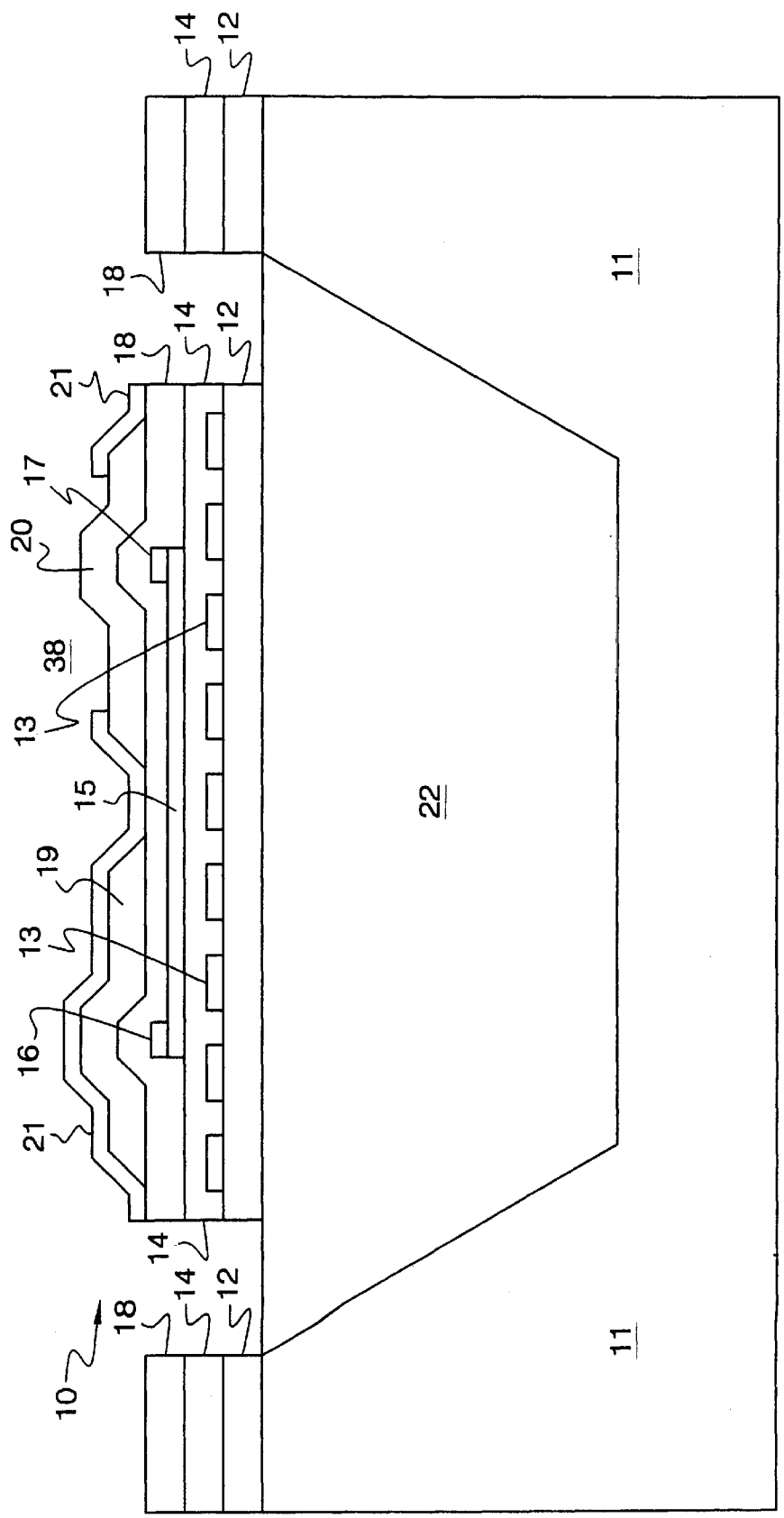
FIGS. 1 and 2 are sectional and plan views of a differential thermal analysis sensor.
Figure 2:
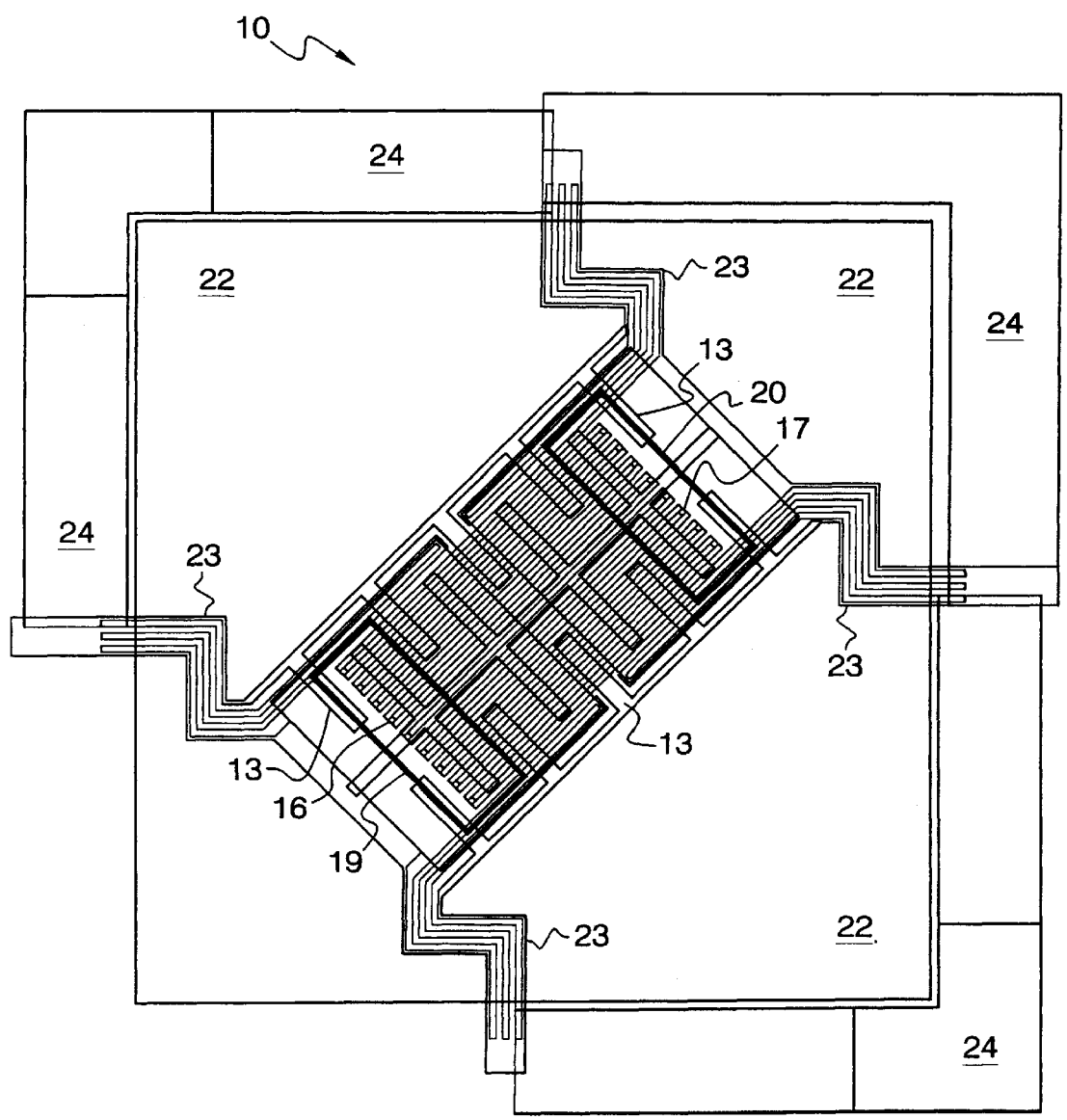

FIGS. 1 and 2 are cross sectional and plan views, respectively, of a differential thermal analysis sensor, membrane or calorimetric device configuration 10. FIG. 1 shows the laminated thin film microstructure suspended over etch pit 22 in silicon 11. The lamination contains a heater 13, differential thermocouple pairs 15, a gas-sensitive active coating 20 and a gas-insensitive (i.e., shielded) active coating 19. The plan view shows how thermocouple pairs 15 overlay heater 13 and are configured relative to etch pit 22. The active components are isolated from one another by dielectric layers 12, 14 and 18. Dielectric 21 also isolates active element 19 from the ambient environment.

FIG. 1 reveals a cross-section of a differential thermal analysis sensor 10. Formed on silicon substrate 11 is a dielectric or silicon nitride layer 12. Formed on layer 12 are laminated heating elements 13. Element or elements 13 may be made from platinum or titanium nitride. Element or elements 13 may instead be placed on another layer of structure 10 co-planer with thermocouple 15. Elements 13 and portions of layer 12 are covered by another silicon nitride layer 14. Formed on layer 14 is an array of thermocouples 15 having junctions 16 and 17. One length or leg of thermocouple 15 is 60/40 nickel-iron and the other length or leg is chromium. Each pair of thermocouple leads, lengths or legs alternate in material as they lay on layer 14, and the pairs of leads having differing materials are connected together as junctions 16 and 17. Another nitride layer 18 is formed on thermocouples 15, including junctions 16 and 17, and on portions of layer 14 not overlapped by an element 13. An active material 19 is formed on layer 18 in an area proximate to junctions 16. A second active material 20 is formed on layer 18 in another area proximate to junctions 17 but apart from active material 19. A silicon nitride passivation layer or coating 21 is formed on material 19. Layer 21 covers active material 19 so as to seal it from the ambient environment. On the other hand, active material 20 is exposed to the ambient environment of device 10. This non-exposure and exposure are a key to differential sensing. The silicon, under layer 12, is removed by a form of etching thereby resulting in a pit 22 in substrate 11 below layer 12. Layer 12 is suspended over pit 22.

FIG. 2 is a plan view of device 10. Layers 12, 14 and 18, along with heater elements 13 and thermocouples 15, with junctions 16 and 17, are suspended over an etch pit 22 by supporting arms 23 that support conducting leads from the edges or border 24 of the chip of device 10 for heater elements 13 and thermocouples 15. In the figure, there are eight junctions 16 under passivated active material 19 and eight junctions 17 under exposed active material 20.

Figure 3A:
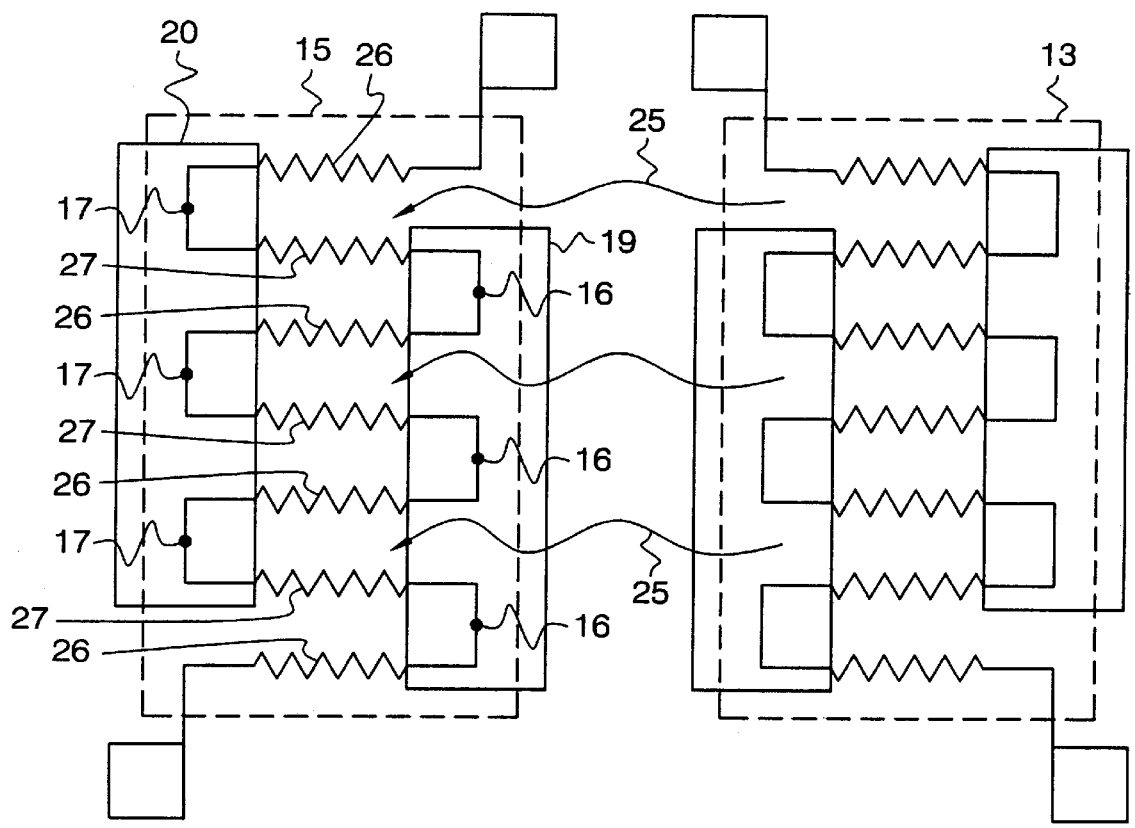
FIG. 3a is a schematic of the heater and thermocouples of the sensor.

FIG. 3a is a schematic of thermocouples 15 and heater 13. Heater 13 provides heat to materials 19 and 20, and thermocouples 15. Legs or length 26 are composed of the 60/40 nickel-iron and legs or lengths 27 are composed of chromium. Temperature sensing thermocouple junctions 16 and 17 are connected in series in a differential manner wherein interconnected junctions 16 and 17 have common legs 26 and 27, such that the temperature sensed by junctions 16 proximate to material 19 and the temperature sensed by junctions 17 proximate to material 20, cancel each other for the same temperatures, and indicate only the relative temperature difference or delta between materials 19 and 20. Junctions 16 are reference thermocouple junctions. Junctions 17 are the detection thermocouple junctions for sensing catalytic or latent heat.

Figure 3B:
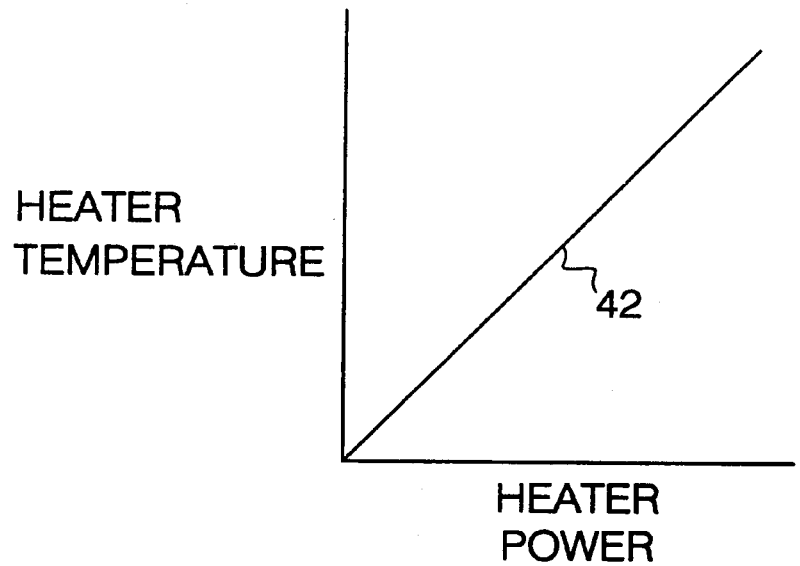
FIG. 3b is a graph of heater power versus temperature of the sensor.
Figure 3C:
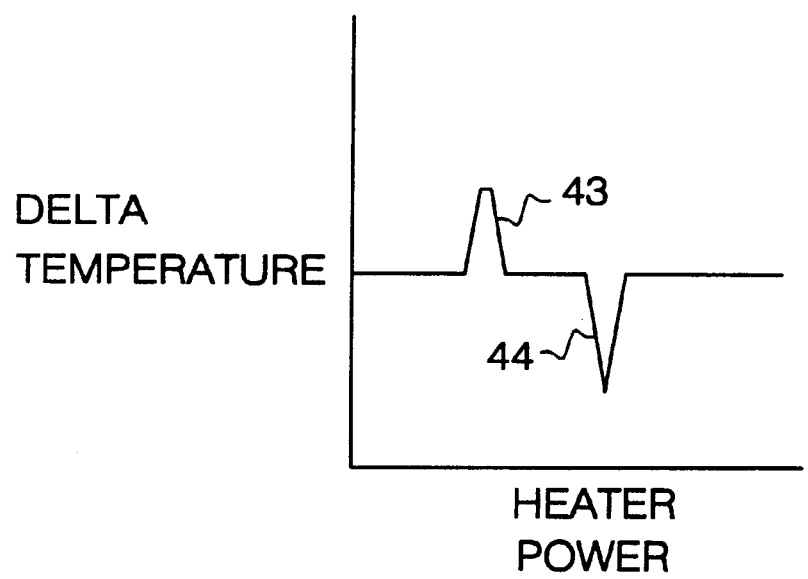
FIG. 3c is a graph of the delta temperature between two sets of thermal junctions and heater power.

Curve 42 of FIG. 3b shows the linear relationship between heater 13 power and temperature. The graph of FIG. 3c shows the delta temperature between junctions 16 and 17 and heater power. Curve 43 reveals an exothermal reaction and curve 44 reveals desorption at material 20.

Microcalorimeter 10 is a low thermal mass, low thermal conductivity device for measuring differences in enthalpy of interaction for coated and uncoated devices. Active material coatings may vary significantly but can include common gas chromatograph materials (e.g., CARBOWAX, $SiO_2$ and ZEOLITE) and catalytic materials (e.g., Pt, Pd and $WO_3$). Because of the very low thermal mass and low power features, measurements of small energy consumption differences may be measured.

The enthalpy of the interaction with active material 20 include desorption of material from the device surface or a coating on the surface (e.g., water vapor from polyimide), catalytic (enothermic or endothermic) energy of reaction from the surface (e.g., $CO+CO_2<>CO_2+energy$), or desorption of material with non-thermal stimulation (e.g., photo stimulation, visible, UV and IR light).

Properties of coatings may include absorbing specific materials and controllably desorbing them (e.g., heat or light), or generating or consuming energy by catalyzing a reaction from gases in the ambient.

Figure 4:
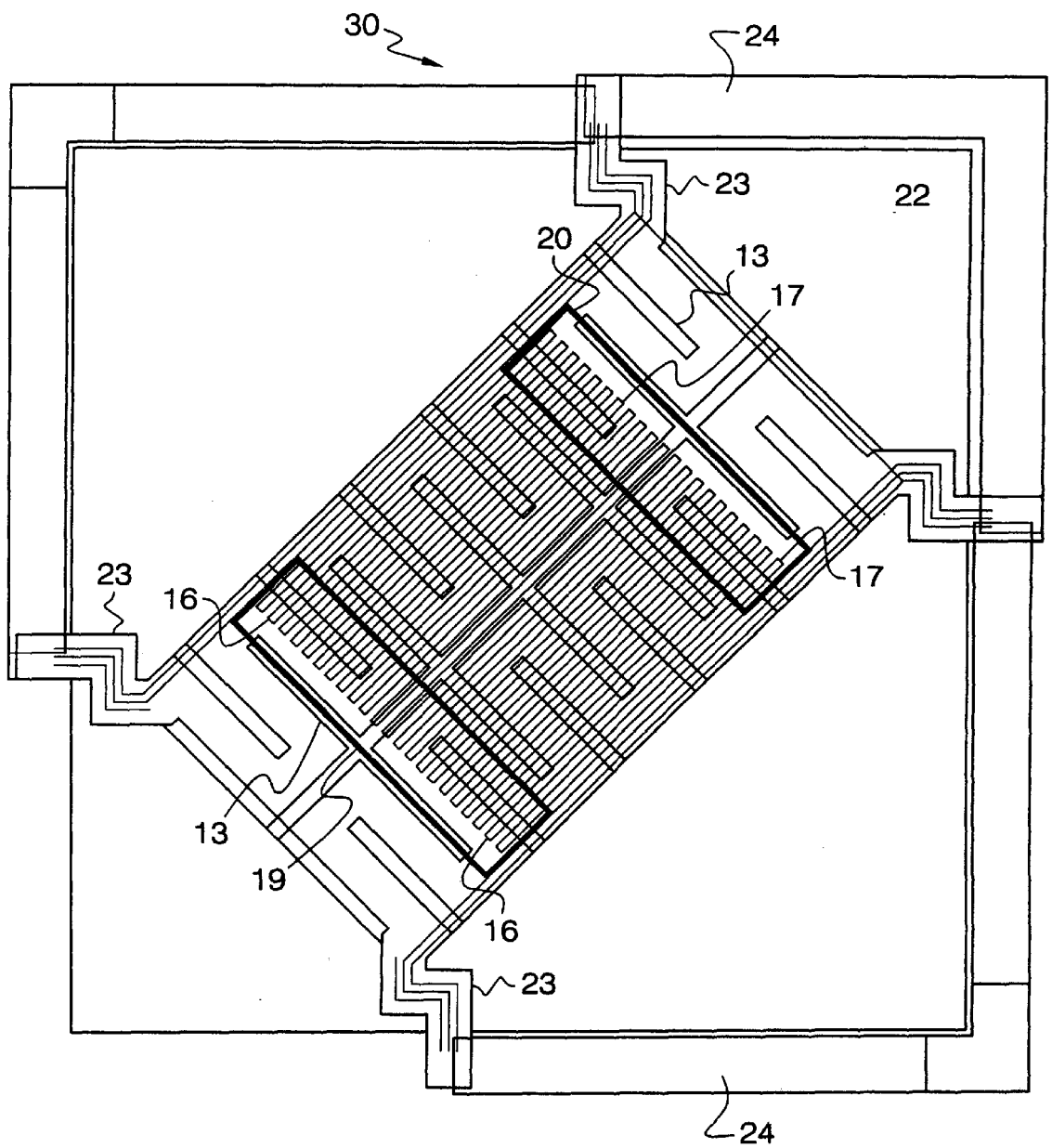
FIG. 4 is another layout of the sensor.

Device 30 of FIG. 4, like device 10, is configured to actually measure the difference in temperature across one structure. The junction monitor temperature differences are caused by coated end 19 of the microstructure relative to uncoated end 20. Devices 10 and 30 have thermally isolated areas between 0.03 $mm^2$ and 0.19 $mm^2$ for a thickness of one micron with a thermal isolation of about 70 microwatts per degree Centigrade.

Thermocouples 15 generate 65 microvolts per junction pair per degree C. difference in temperature. Thermocouples also generate about 3 ohms per laid-out square (length/width) of material that contributes to noise. The noise in these materials has been noted in infrared devices to be dominated by Johnson noise. The thermocouple material has been shown to work up to 350 degrees C. The material used for heater 13 is stable up to at least 1000 degrees Kelvin, which exceeds the needs of this application.

For these sensing devices, a heat pulse is applied to the sensing membrane of the sensor through the heating resistor, and the temperature response of the uncoated end 20 relative to the coated end 19 is recorded. The temporal profile of each input heat pulse can be selected to maximize the analytic information extracted from the sensor. The pulses may be simple square waves having a duration of 100 milliseconds and a voltage amplitude sufficient to raise uncoated end 20 temperature about 10 degrees C. These pulses may be used to detect chemical warfare (CW) agents. The baseline temperature and the shape of the pulses can be modulated to modify the interaction of the analyte (i.e., the substance or material to be detected and/or identified) with sensor surface 20. Due to different thermal and kinetic properties of sorbed vapors and the ambient, different analytes will have different optimum pulse shapes. The range of possibilities for pulse shaping depends only on the thermal time constant of the sensor, and physical limitations of the sorbent coatings. A large range of temperature profile possibilities increases the chance that the array of modulated sensors 10 will be selective for multiple CW agents. Each modulated sensor 10 in the array has an optimum heating profile, depending on the thermal properties of the analyte and the sorbent coating and their interactions. Tuning each sensor 10 in the array with a different thermal profile maximizes sensitivity and selectivity for target analytes.

Advantages of applying a modulation approach to silicon based sensors 10 is the approach that includes anti-drift and self-cleaning mechanisms. The effect of drifting background can be minimized by comparing the signal during the pulse to the baseline response of the sensor. As the baseline response shifts due to temperature, electrical or aging effects, the analyte response can be referenced to the changing background, and still be calibrated. As sorbent coatings begin to foul, the sensitivity drops. The problem normally requires recalibration of the sensor system 10 or replacement of the sensitive elements 20. In a pulsed sensor, applying a relatively high temperature pulse to the sorbent coating drives off the sorbed interfering species. This returns sensor 10 to its standard baseline and increases the sensor's lifetime.

In summary, thermal modulation promotes a zero order heat flux sensor to a first order sensor by providing temporal information about the system, allowing analyte discrimination due to sorption/desorption dynamics during a change in the temperature of the sensor. Specific analytes, such as CW agents, can then be identified and quantified in the presence of interferents by building chemometric models of the system for expected analytes at multiple concentrations. The profile of the temperature modulation can take on any form, limited only by the thermal time constant of the device. The shape of the sorption/desorption curves depends on many parameters, including the input pulse shape, thermal conductivity of the analyte in the gas phase, heat capacity, enthalpy of vaporization, diffusivity of the analyte, and the effect of any sorbent interaction between the analyte and sensor 10.

Figure 5:
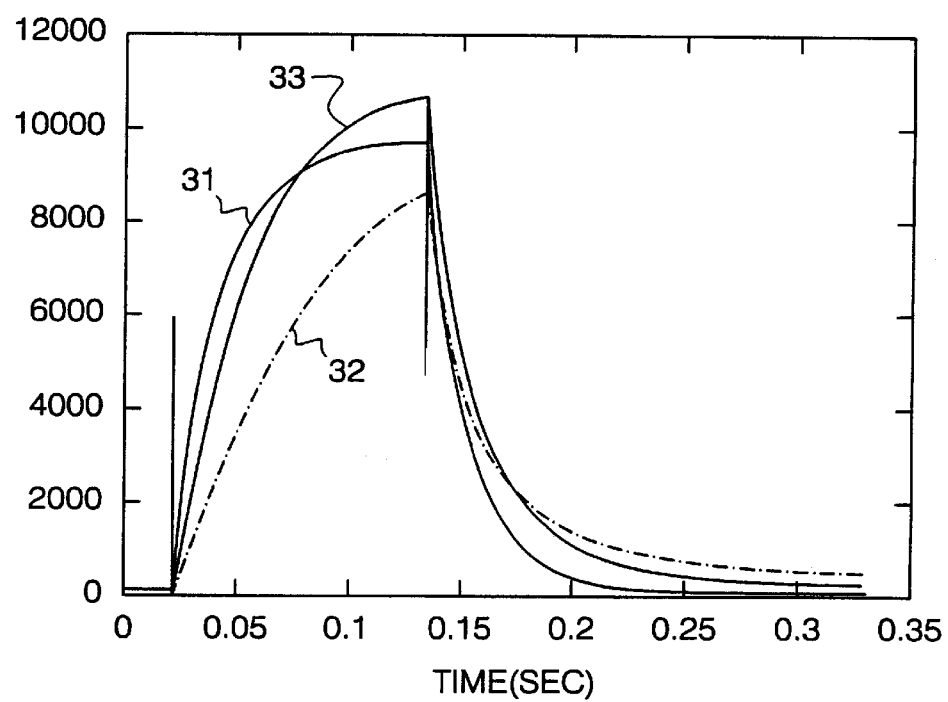
FIG. 5 shows sensor responses that differentiate between various gases.

Tests have been focused on characterizing a thermally modulated microcalorimeter 10 without involving the complexity of interactions contributed by the addition of a sorbent phase. Sensor 10 was mounted in a temperature-controlled cell, and saturated vapors of chloroform and acetone in air were introduced to the sensor. Integrated heater 13 was pulsed with a square wave, and the temperature of membrane 20 monitored over the life of the pulse. The sensor 10 response under these conditions shows that monitoring the temporal response of the sensor can differentiate between gases with different thermal and chemical properties, as shown in FIG. 5. This figure shows bare sensor 10 response to saturated organics. Curve 31 shows amplitude of sensor response versus time for air. Curves 32 and 33 show the responses for chloroform and acetone, respectively. The sensor 10 response is broken into three distinguishable parts—the response directly after the pulse is applied, the magnitude of the response after thermal equilibrium has been reached, and the thermal decay. The initial response depends on the heat capacity and kinetics of the analyte, while the equilibrium value describes the thermal diffusivity. The decay is a combination of these effects.

Figure 6:
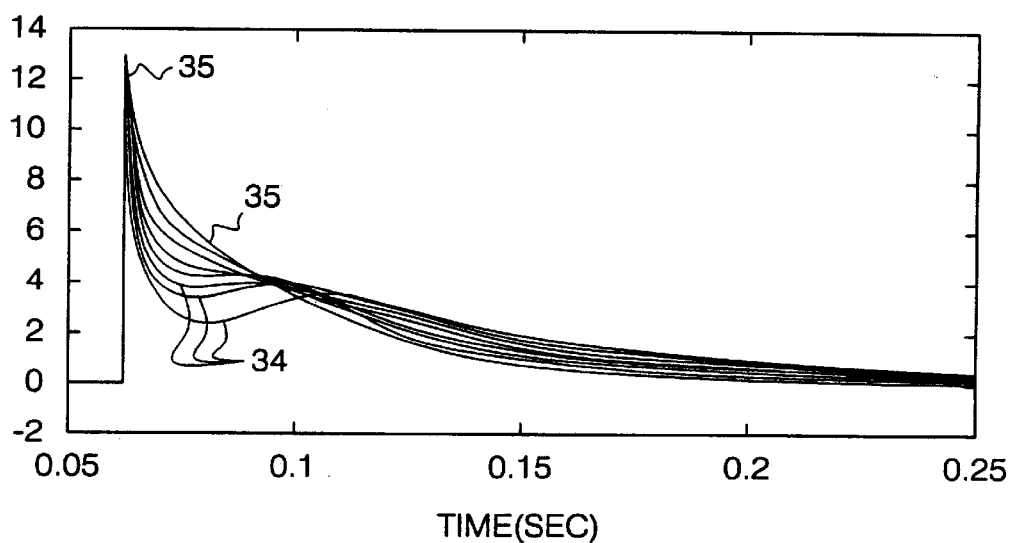
FIG. 6 shows first derivative of sensor responses for air and various concentrations of mixed chloroform saturated nitrogen with a dilution stream.

The transient mode of sensor 10 operation can also be used to measure analyte concentration in the gas phase. Chloroform test gases from 2000 ppm to saturated vapor pressure were created using a flow system that quantitatively mixed chloroform saturated nitrogen with a dilution stream. The concentration effect on sensor 10 is highlighted by looking at the slopes of dynamic sensor responses 34 for the impulse, as shown in FIG. 6. Curves 34 with the greater dip or lag reveal higher concentrations of chloroform. Curve 35 displays sensor 10 response for air. This figure shows the first derivative of the sensor responses to chloroform samples. Principal component analysis (PCA) of the entire sensor 10 response showed that this phase lag effect is linear with concentration. Estimating the sensing area to be 1 mm², and making an approximate estimate of the penetration depth of the heat pulse at 1 mm, the mass detection limit for the chloroform calibration was calculated to be 10 $\mu$g. It should be re-emphasized here that this occurs with no sorbent coating on sensing element 20.

Figure 7:
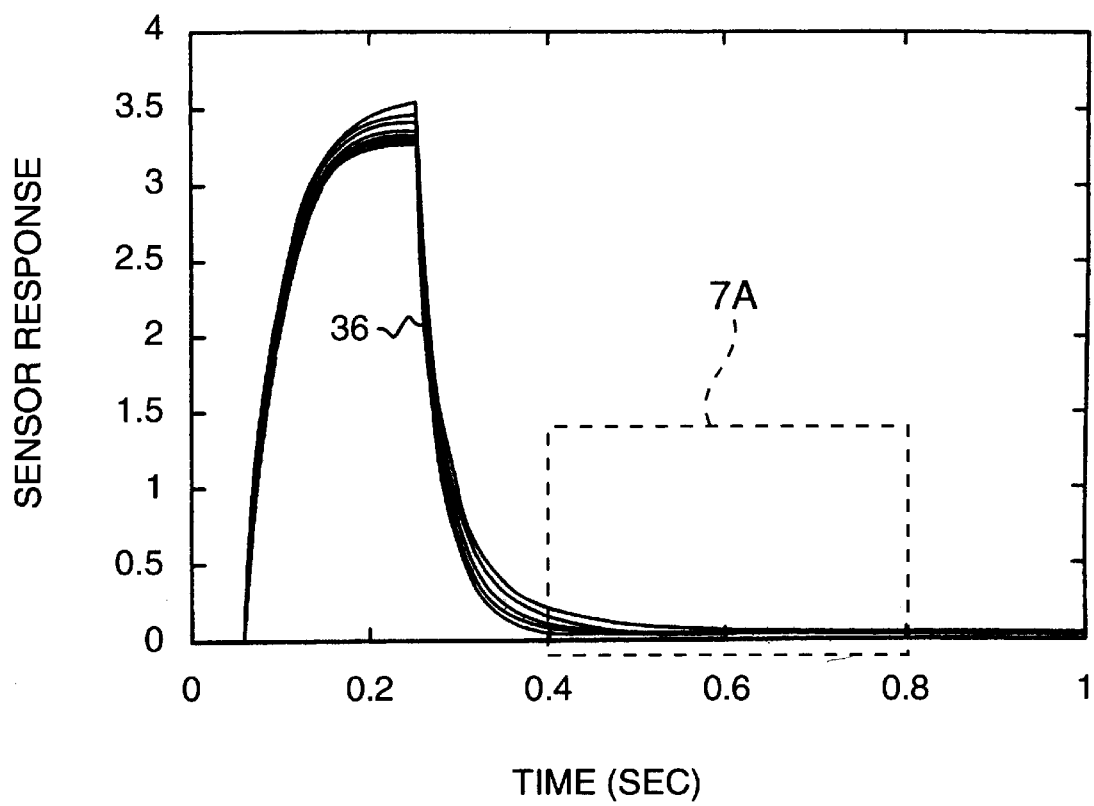
FIG. 7 shows sensor responses to various concentrations of chloroform saturated air.
Figure 7A:
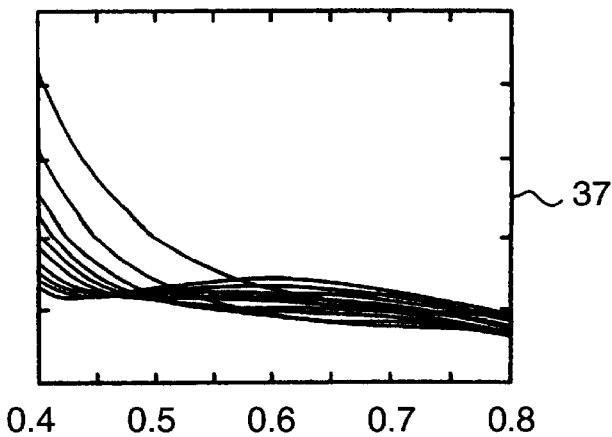

Data from coated sensors resulted from a study of chloroform detected on a CARBOWAX 20M-coated microcalorimeter element 20. The CARBOWAX was dissolved in chloroform, and spray coated onto material 20 surface of sensor 10. Responses 36 of sensor 10 to chloroform saturated air is shown in FIG. 7. This figure shows the sensor response to the chloroform concentration series. At a first glance, the coated material 20 of sensor 10 response looks similar to the response of a bare material 20 of sensor 10 to chloroform, with the phase delay magnified in area 37. However, the interesting part of the sensor response comes well after the heat pulse has been terminated. The temperature of the sensor surface comes to a minimum, then heats up slightly, and then returns to baseline (shown in the inset of FIG. 7). The magnitude of this secondary response was proportional to the concentration of chloroform in the vapor phase, and corresponds to the re-establishment of the concentration equilibrium between the gas and sorbent phases. The magnification of the phase delay and the secondary effects on application of a sorbent phase may be exploited to increase the sensitivity and selectivity of the present technique. This effect is indicative of the type that should be explored, one where the enthalpy of phase change between the gas and sorbent phase can be measured as a function of temperature. The reverse reaction, enthalpy of evaporation, occurred in the heating side of the curve.

The next step was to calibrate sensor 10 for each of two gases in a binary mixture. The sensor was heat pulsed in the presence of a concentration series of chloroform and hexane individually. Calibration models were built on each of the concentration series. Binary mixtures of the two solvents were made with separate bubblier systems, mixed, and the sensor 10 response monitored. The concentration of the mixtures were then predicted based on the response of the sensor to the individual species. The whole data set, including the calibration series, was predicted using each model. This prediction shows that the model built on the chloroform data set predicts nearly zero hexane, and the model built on the hexane data predicts nearly zero chloroform. The mixtures fall somewhere in between, and are predicted by sensor 10 within ten percent of their actual values for both components.

Thermal modulation also yields some selectivity advantages in the form of kinetic selection. The temperature gradient produced over the face of heated sensor 10 forces the gas out of equilibrium. The non-steady state condition gives rise to mass transfer, and thus heat transport, away from sensor 10. The relative diffusivities of different components give rise to compositional gradients above the sample, which in return effect the rate of heat transport over time. The heat flux away from sensor 10 is thus dependent on the physical properties of the gas phase, and develops in time after a heat pulse. Monitoring the sensor 10 response during this heat pulse provides dynamic information on the analytes in the gas phase, e.g., kinetic selectivity.

The requirements for a sensing material 20 allow the sensor to respond rapidly, reversibly, and reproducibly. Without these characteristics, pattern recognition algorithms and calibration models cannot be developed that will be of any use in evaluating future chemical exposures. The application imposes additional requirements on individual sensing materials and on the set of sensing materials in the array of sensors 10. One or more of the materials 20 must yield sensors 10 with sufficient sensitivity, while the array of materials must provide sufficient selectivity.

The sensing 10 platform (i.e., the type of sensor and its transduction mechanism) imposes additional requirements. Optical sensors require materials exhibiting optical changes; chemiresistor sensors require materials exhibiting changes in electrical conductivity; and acoustic wave sensors measure mass increase. Finally, the material must be suitable for deposition on the sensor as a thin film. The application of films to very small domains of microfabricated structures is a challenge that is becoming increasingly important as newer smaller sensor designs are developed.

Figure 8:
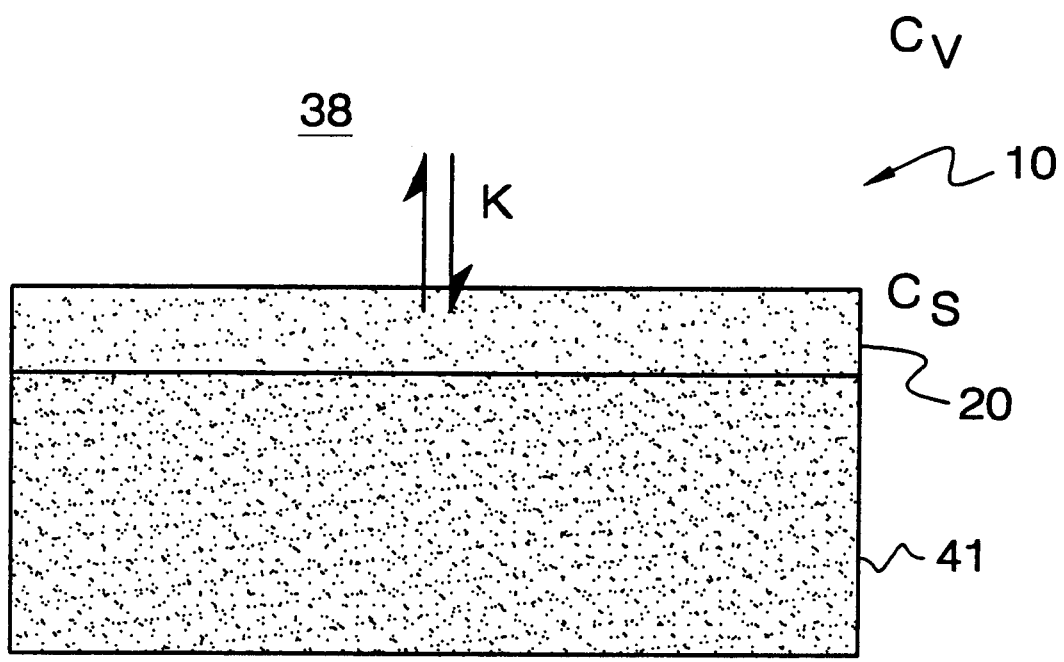
FIG. 8 illustrates a generic chemical sensor.

The first step in obtaining a sensor signal is the partitioning of the analyte from the medium being analyzed into or onto the surface of sensor 10, usually into a chemically selective sensing material. This concept is shown in FIG. 8. This figure shows a generic illustration of a chemical sensor. This approach is applicable to various types of sensors using absorbent thin films. Volume 38 includes the analyte molecules out in the ambient medium. Layer 20 is the sorbent sensing material. Portion 41 is the sensor device which is sensor 10 minus sensing material 20. The applied thin film of a chemically selective layer collects and concentrates analyte molecules at the sensor's surface. In this approach, the sensor device by itself cannot directly detect the analyte molecules out in the medium being analyzed. Rather, the sensor device typically detects changes in the physical properties of the sensing material when the analyte is present in the sensing material. The generation of a measurable analytical signal in response to the sorbed analyte is called transduction. The microcalorimetric sensors will detect the thermal properties of the layer interacting with the sorbed species as these are perturbed by the thermal pulse.

The equilibrium distribution of a compound between two phases is given by the partition coefficient, K. For example, the partition coefficient for partitioning between the gas phase 38 and a sorbent phase 20 is given by the partition coefficient, defined in equation 1 where $C_s$ represents the concentration of the vapor in the sorbent phase 20 (the polymer in the case of a polymer-coated sensor), and $C_v$ represents the concentration of the vapor in the gas phase 38. The partition coefficient provides a thermodynamic measure of the strength of sorption. It is related to the standard Gibbs free energy of solution of a gaseous solute, $\Delta G_s^o$, by equation 2, where the standard states are unit concentration in the gas phase and unit concentration in solution.

$$K = C_g/C_v \qquad (1)$$

$$\Delta G_S^O = -RT\ln K \qquad (2)$$

$$S = f(C_v) \qquad (3)$$

$$S = f(C_g) \qquad (4)$$

$$S = f(KC_v) \qquad (5)$$

The relevance of the partition coefficient to a sensor's response can be seen directly in equations 3–5, using gas phase sensing as an example. The response, S, of a chemical microsensor is empirically measured as a function of the gas phase 38 vapor concentration ($C_v$), as set out in equation 3.

However, sensor device 41 actually responds to the concentration of analyte sorbed ($C_s$) in selective layer 20, as set out in equation 4. Therefore, it follows that the sensor's response is related to $KC_v$, as set out in equation 5. Equation 5 provides a very general relationship that illustrates the key role of sorption and the partition coefficient in the response of a chemical sensor. The influence of the sorption step is given by $KC_v$, while the transduction step is accounted for by the function operating on $KC_v$.

Fast reversible sensor responses are obtained if the polymer is amorphous and its static glass-to-rubber transition temperature is below the sensor's operating temperature. The greater thermal motion of polymer chain segments of a rubbery (as opposed to glassy) polymer and the greater free volume allows rapid diffusion of vapors through the material and provides access to sites for interactions. Acoustic wave microsensors using rubbery polymers have response times of a few seconds or less. By contrast, glassy polymers can lead to response times that are orders of magnitude slower. Consequently, the static glass-to-rubber transition temperature is an important criterion in the design or selection of a polymer for a chemical vapor sensor. Rapid diffusion processes will be important in developing sensors based on the microcalorimetric method with short thermal pulses.

The interactions governing sensor responses are solubility interactions and these can be investigated with linear salvation energy relationships (LSERs). The types of solubility interactions that occur between neutral organic species include dispersion interactions (also known as London forces or induced-dipole/induced-dipole interactions), dipole/induced-dipole interactions (also known as induction interactions), dipole/dipole interactions (also known as orientation interactions), and hydrogen-bonding interactions. (The general term van der Waals interactions includes dispersion, induction, and orientation interactions, as well as electrostatic interactions involving charges and polarizable or dipolar species.)

Usually, multiple interactions occur simultaneously. The strengths of the various solubility interactions, and hence the strength of sorption, depend on the respective solubility properties of the vapor solute and the polymer solvent. These properties, which include polarizability, dipolarity, hydrogen-bond basicity, and hydrogen-bond acidity, are determined by chemical structure. Maximum sensitivity is achieved by maximizing all the interactions that can occur between a target vapor and a polymer selected or designed to absorb that vapor. This approach maximizes the partition coefficient and hence the amount of vapor sorbed for a given vapor concentration. For example, a basic vapor will be most strongly sorbed by a polymer that is a strong hydrogen bond acid. To maximize selectivity for a particular type of vapor, it is best to select a polymer that emphasizes a particular interaction. This limits the types of vapors with which the polymer will have strong interactions. A systematic approach for considering solubility interactions between vapors and polymers involves the use of linear salvation energy relationships (LSERs). These relationships involve salvation parameters that quantify the solubility properties of vapors and LSER coefficients that characterize the complementary solubility properties of sorbent polymers. These parameters and relationships have proven to be useful in many aspects of sensor development, including understanding properties of vapors to be detected; characterization of sorbent polymer properties; evaluation of the relative strengths of the interactions governing sorption between vapor/polymer pairs; prediction of partition coefficients; estimation of sensor responses; elucidation of transduction mechanisms; and strategies for sensitivity, selectivity, and polymer design.

Figure 9A:
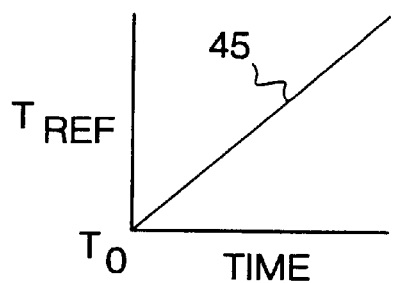
FIGS. 9a and 9b are graphs showing the temperature responses to a constant power pulse in the reference leg and in the active leg, respectively, of the sensor.
Figure 9B:
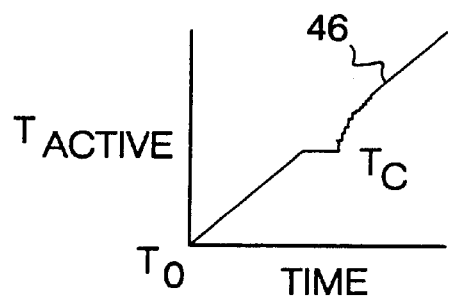
Figure 9C:
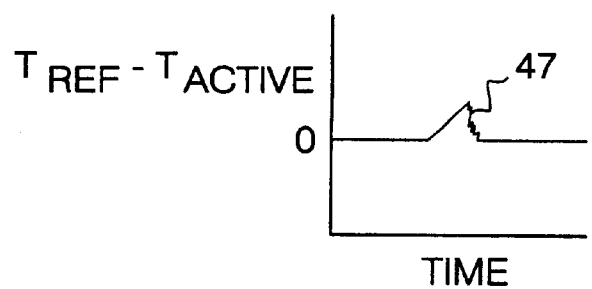
FIG. 9c is a graph showing the difference between the temperature responses of FIGS. 9a and 9b.

The following is a mathematical model of ultimate sensitivity to estimate sensitivity based on the energy balance in the microstructures using the parameters of the standard microbridge sensor. FIGS. 9a, 9b and 9c are graphs having curve 45 showing the temperature response ($T_{reference}$ or $T_r$) to a constant power pulse in the reference material or leg 19, curve 46 showing the temperature response ($T_c$) in the active material or leg 20 having a temperature ($T_{active}$ or $T_a$), and curve 47 showing the temperature difference ($T_r - T_a$) between the two materials or legs as shown in FIGS. 9a and 9b. The response temperature difference ($T_r - T_c$) over time is the resultant signal having the information about the substance detected. The actual signal will be an electrical signal representing the response temperature difference.

The equations governing the energy balance of the two legs are given by concentration of analyte sorbed gas phase 38 vapor concentration.

$$L\frac{dm}{dt} + (T_c - T_0)G = P \quad \text{(active)}, \tag{6}$$

$$MC_p\frac{dT_r}{dt} + (T_r - T_0)G = P \quad \text{(reference)}, \tag{7}$$

where L is the latent heat of desorption of the adsorbed gas, M is the mass of the adsorbed gas, G is the conductance, $C_p$ is the specific heat, $T_c$ is the temperature response of the gas phase 38 vapor concentration ($C_v$), that is, of active material 20, $T_r$ is the temperature response to a constant power pulse in reference material 19, and t is time. Equations (6) and (7) are rewritten in terms of $\tau = T_r - T_c$ as $$L\frac{dm}{dt} = p \quad \text{(active)}, \tag{8}$$

$$MC_p\frac{d\tau}{dt} + \tau G = p, \quad \text{(reference)}, \tag{9}$$

where $\rho$ is the incremental power.

Integrating Equation (9), for constant power, gives $$\tau = \frac{p}{G}(1 - e^{(-G/MC_p)t}) \approx \frac{p}{MC_p}t, \tag{10}$$

where the latter approximation applies to short times, i.e., $t < MC_p|G$.

Equation (8) can be rewritten as $$L\frac{dm}{d\tau} = p\frac{dt}{d\tau} = MC_p\frac{p}{p - \tau G}, \tag{11}$$

Using the short time approximation from Equation (10) implies $\tau G < \rho$, which gives $$dm = \frac{MC_p}{L}d\tau. \tag{12}$$

A differential temperature of $d\tau$ gives a differential voltage between the two sensing legs. For two identical sensing legs comprising n thermocouples one obtains $$dV = n\alpha_T d\tau = \frac{Ln\alpha_T dm}{MC_p}, \quad (13)$$

where $\alpha_T$ is the thermoelectric coefficient of thermocouples. The noise voltage is given by $$dV_n = \sqrt{4k_B T_c R \Delta f}, \quad (14)$$

which gives, for noise equivalent mass difference (NEMD), $$dm = \frac{\sqrt{4k_B T_C R \Delta f}\, MC_p}{Ln\alpha_T}. \quad (15)$$

One now estimates the NEMD for "order of magnitude" estimates of various parameters applicable to microbridge. From previous measurements on the microbridge it is known that, $G=3.3\times10^{-5}$ W/° C., $M=6.7\times10^{-8}$ g using dimensions 1.4 $\mu$m×1.5 $\mu$m and a density of 3.2 g/cc, $C_p=0.7$ J/g.° C., $\alpha_T=66\times10^{-6}$ V/° C., n=9 and R=900. Note that at room temperature $T_c=300$K, which gives Ldm=$9.77\times10^{-13}$ Jl/$\sqrt{Hz}$. To further estimate the NEMD a value for latent heat is needed. In the absence of data for desorption of gases from polymer coatings one can use the latent heat of evaporation at the boiling point of water. It is $L=4.067\times10^4$ J/mole. The NEMD is $$dm = 2.40\times10^{-17}\ \text{mole}/\sqrt{Hz}$$

$$= 1.45\times10^7\ \text{molecule}\sqrt{Hz}$$

$$= 4.32\times10^{-16}\ g/\sqrt{Hz},$$

where, for water, 1 mole=18 g.

Using the same calculations to estimate agent response one can generate the table below. The results in the following table support the present approach.

| Chemical | Latent Heat of Vaporization (J/gm) | Mole weight | NEMD (molecules/root-hz) | NEMD (gms/root-hz) | PPB Sensitivity |
| --- | --- | --- | --- | --- | --- |
| Water | 2259.0 | 18 | $1.45 \times 10^7$ | $4.32 \times 10^{-16}$ | 0.02 |
| Mustard Agent HD | 393.3 | 159 | $1.5 \times 10^9$ | $3.95 \times 10^{-13}$ | 2.2 |
| Nerve Agent GD (Soman) | 301.25 | 182 | $1.96 \times 10^9$ | $5.9 \times 10^{-13}$ | 2.9 |
| Nerve Agent GB | 334.72 | 140 | $1.76 \times 10^9$ | $4.09 \times 10^{-13}$ | 2.6 |

*Noise limit of sensitivity in parts per billion assuming that all chemical within a 250 microliter volume has been adsorbed into the sensor's film assuming 100 Hz circuit bandwidth and Johnson noise limited performance.

Figure 10:
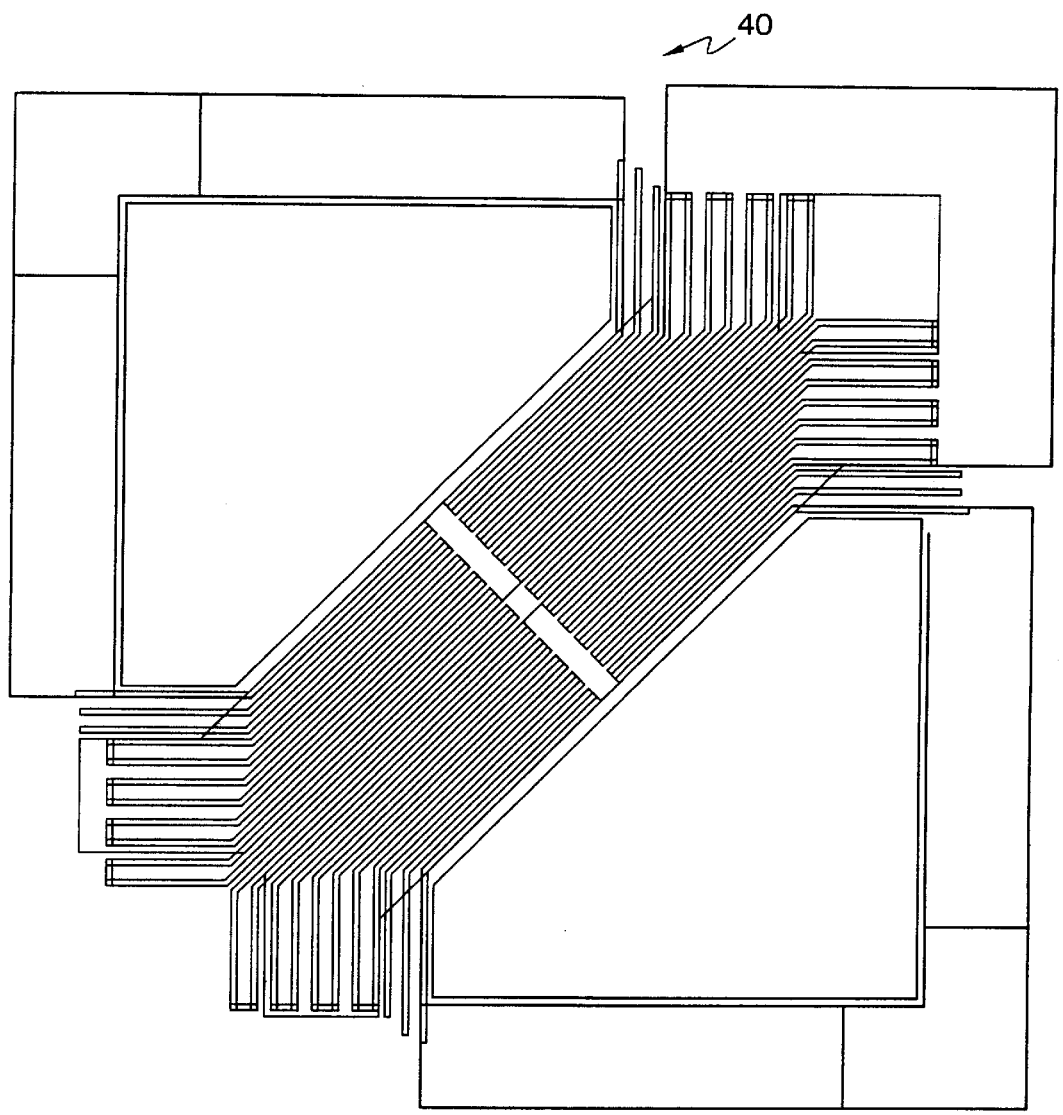
FIGS. 10 and 11 show sensor configurations with the junction sets of the active and inactive legs proximate to each other.
Figure 11:
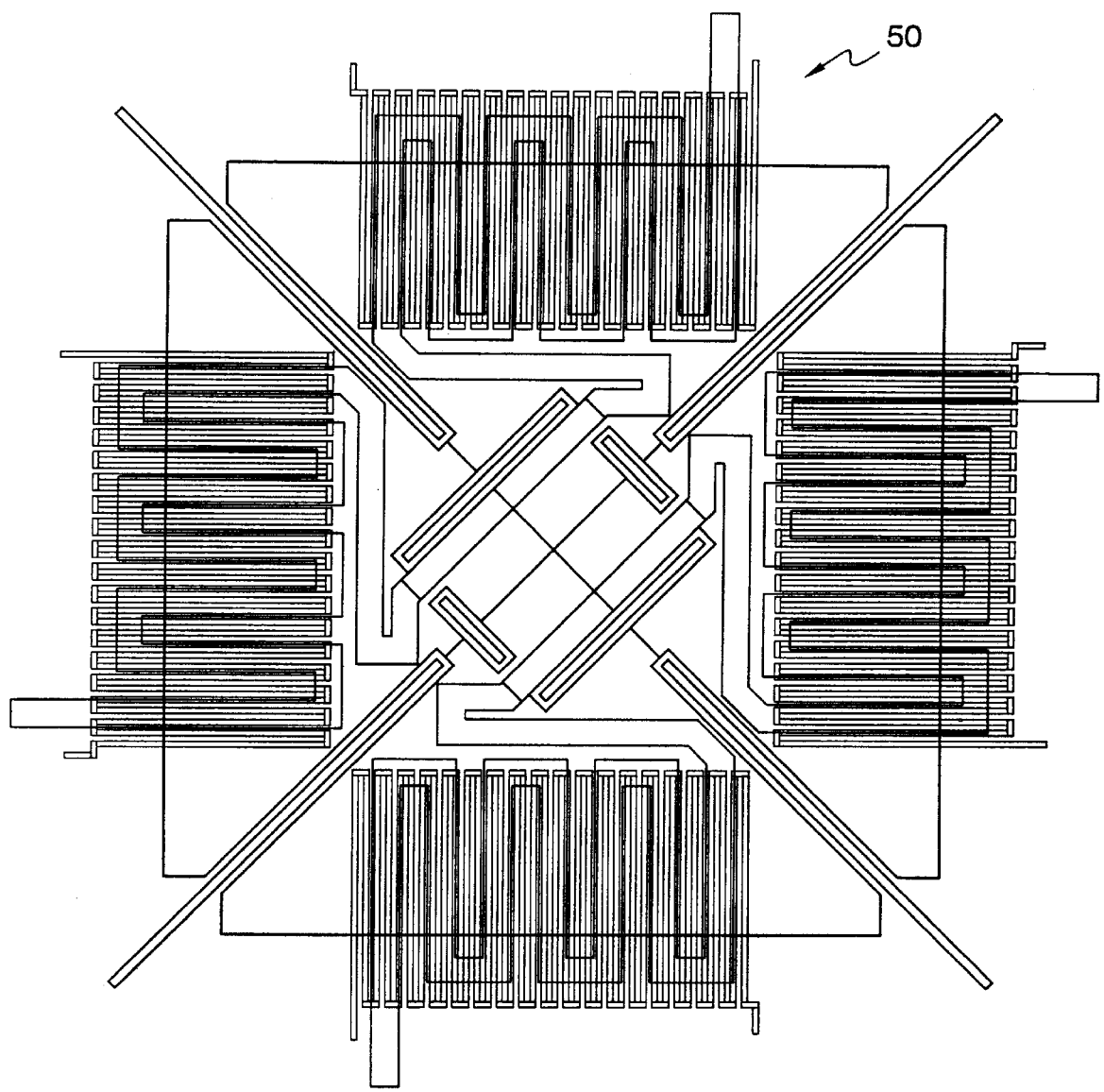

Devices 40 and 50 of FIGS. 10 and 11, respectively, differ from devices 10 and 30 in that they are designed to measure the temperature of the microstructure relative to the silicon heat sink reference junctions. In use, they would be used in pairs with the voltage of a coated bridge being subtracted from an uncoated bridge. These devices 40 and 50 have thermally isolated areas of between 0.04 mm² and 0.16 mm² for a thickness of one micron with a thermal isolation of about 200 microwatts per degree C.

Figure 12:
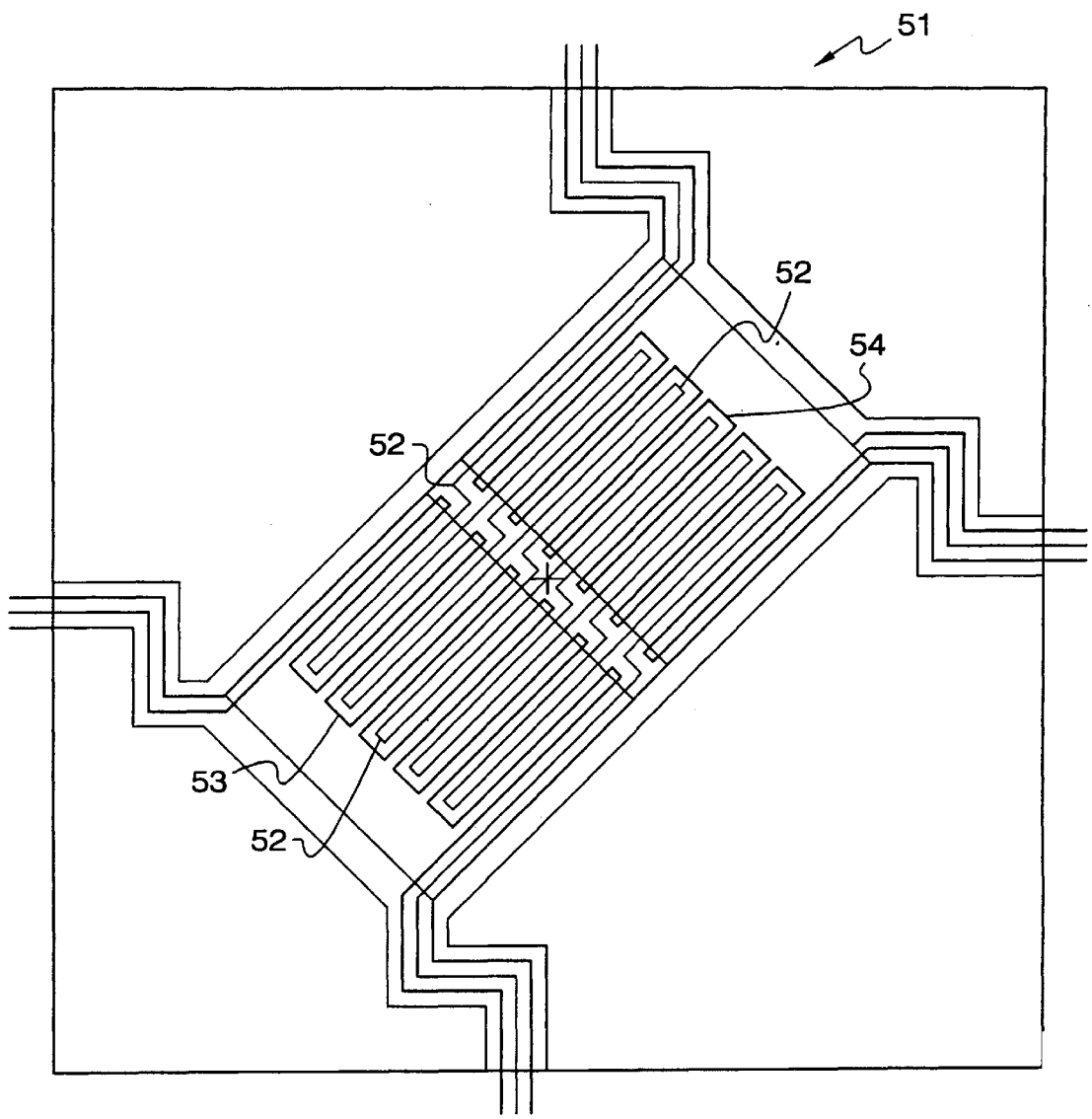
FIG. 12 reveals a resistive temperature sensor version of the differential thermal analysis sensor.

FIG. 12 reveals a resistive temperature sensor (detector) (RTD) version of a differential thermal analysis (DTA) sensor 51. A heater 52 is intertwined with two temperature sensors 53 and 54. On each edge, lower right and upper left, there are single thermocouples to help monitor heater temperature control, but this can also be done using the heater resistance itself or even a passivated temperature sensor. In device 51, all of the resistors are co-planer rather than laminated. There is a temperature sensor for the passivated side (upper right) and a temperature sensor for the unpassivated side (lower left). The most likely mode of operation is having the two temperature sensors in a wheatstone bridge to monitor the temperature difference between them while controlling the microbridge temperature using the heater and bridge temperature sensors. A number of sensors 51 can be formed into an array.

What is claimed is:

1. A differential thermal analysis sensor comprising:
   a substrate having a pit;
   a first dielectric layer proximate to the pit;
   a heating element formed on said first dielectric layer;
   a second dielectric layer formed on said heating element and said first dielectric layer;
   a first set of thermocouple junctions formed on said second dielectric layer;
   a second set of thermocouple junctions formed on said second dielectric layer;
   a third dielectric layer formed on said first and second sets of thermocouple junctions;
   a first active layer is formed proximate to said first set of thermocouple junctions;
   a second active layer is formed proximate to said second set of thermocouple junctions; and
   a fourth dielectric layer is formed on said first active layer.

2. The sensor of claim 1, wherein the first and second sets of thermocouple junctions are interconnected so that an output of the junctions indicates a temperature difference between the first and second active layers.

3. The sensor of claim 2, wherein the thermocouple junctions are interconnected such that each junction of one set has at least one lead that is a lead for a junction of the other set of thermocouple junctions.

4. A differential thermal analysis sensor comprising:
   a thermally isolated microstructure;
   heater within said microstructure; and
   two temperature sensors within said microstructure; and
   wherein:
      said heater and two temperature sensors within said microstructure are substantially co-planar;
      coatings are formed on said two temperature sensors, one passivated and one allowed to thermally interact with an airborne chemical; and said microstructure is formed on a substrate having a single pit therein to provide the thermal isolation.

5. The sensor of claim 4, wherein said temperature sensors are a plurality of thermocouples connected in series.

6. The sensor of claim 4, wherein said temperature sensor is a resistive temperature sensor.

7. A differential thermal analysis sensor comprising:

a thermally isolated microstructure;

a heater within said microstructure; and two temperature sensors within said microstructure; and wherein:

said temperature sensors are laminated over said heater within said microstructure;

coatings are formed on said two temperature sensors; one passivated and one slowed to thermally interact with an airborne chemical; and, said microstructure is formed on a substrate having a single pit therein to provide the thermal isolation.

8. The sensor of claim 7, wherein said temperature sensors are a plurality of thermocouples connected in series.

9. The sensor of claim 7, wherein said temperature sensor is a resistive temperature sensor.

* * * * *